United States Patent
Keiser et al.

(10) Patent No.: US 10,213,217 B2
(45) Date of Patent: Feb. 26, 2019

(54) ADJUSTABLE DRILL DEPTH GUIDE

(71) Applicant: EBI, LLC, Parsippany, NJ (US)

(72) Inventors: Matthew L Keiser, Hillsdale, NJ (US); Scott Harrington, San Jose, CA (US)

(73) Assignee: EBI, LLC, Parsippany, NJ (US)

( * ) Notice: Subject to any disclaimer, the term of this patent is extended or adjusted under 35 U.S.C. 154(b) by 0 days.

(21) Appl. No.: 15/721,028

(22) Filed: Sep. 29, 2017

(65) Prior Publication Data

US 2018/0021049 A1 Jan. 25, 2018

Related U.S. Application Data

(63) Continuation of application No. 14/087,094, filed on Nov. 22, 2013, now Pat. No. 9,801,641.

(60) Provisional application No. 61/731,663, filed on Nov. 30, 2012.

(51) Int. Cl.
*A61B 17/17* (2006.01)
*A61B 90/00* (2016.01)

(52) U.S. Cl.
CPC ........ *A61B 17/17* (2013.01); *A61B 2090/034* (2016.02)

(58) Field of Classification Search
CPC ... A61B 17/17; A61B 17/171; A61B 17/1714; A61B 17/1717; A61B 17/1725; A61B 17/1728
See application file for complete search history.

(56) References Cited

U.S. PATENT DOCUMENTS

| | | | |
|---|---|---|---|
| 606,781 A | 7/1898 | Halperin | |
| 1,831,813 A * | 11/1931 | Levedahl | B23B 49/02 408/112 |
| 4,521,145 A | 6/1985 | Bieler | |
| 4,528,980 A | 7/1985 | Kenna | |
| 5,409,493 A | 4/1995 | Greenberg | |
| 5,746,552 A | 5/1998 | Tsui et al. | |
| 5,810,828 A | 9/1998 | Lightman et al. | |
| 5,993,453 A | 11/1999 | Bullara et al. | |
| 7,131,974 B2 | 11/2006 | Keyer et al. | |
| 7,163,542 B2 | 1/2007 | Ryan | |
| 7,261,499 B2 | 8/2007 | Mathis et al. | |
| 7,422,594 B2 | 9/2008 | Zander | |

(Continued)

OTHER PUBLICATIONS

"U.S. Appl. No. 14/087,094, Final Office Action dated Apr. 28, 2017", 7 pgs.

(Continued)

*Primary Examiner* — Nicholas Woodall
(74) *Attorney, Agent, or Firm* — Schwegman Lundberg & Woessner, P.A.

(57) ABSTRACT

An adjustable drill depth guide includes a first sleeve, a second sleeve and a stop member. The first sleeve includes a longitudinal axis and defines a helical slot disposed about the longitudinal axis. The second sleeve is concentrically arranged relative to the first sleeve and is axially adjustable relative to the first sleeve for adjusting a length of the adjustable drill depth guide. The stop member extends radially from the second sleeve and is disposed in the helical slot. The stop member is selectively received at various positions along the helical slot to positively locate the second sleeve relative to the first sleeve in the axial direction.

19 Claims, 7 Drawing Sheets

(56) References Cited

U.S. PATENT DOCUMENTS

| | | | |
|---|---|---|---|
| 7,442,197 B2 * | 10/2008 | Abdelgany | A61B 17/17 606/96 |
| 7,527,631 B2 * | 5/2009 | Maroney | A61B 90/06 606/102 |
| 8,287,547 B2 | 10/2012 | Martin et al. | |
| 9,801,641 B2 | 10/2017 | Keiser et al. | |
| 2005/0222571 A1 | 10/2005 | Ryan | |
| 2006/0264955 A1 | 11/2006 | Abdelgany | |
| 2009/0318927 A1 * | 12/2009 | Martin | A61B 17/1764 606/96 |
| 2010/0094216 A1 * | 4/2010 | Yue | A61M 5/46 604/117 |
| 2014/0155905 A1 | 6/2014 | Keiser | |

OTHER PUBLICATIONS

"U.S. Appl. No. 14/087,094, Non Final Office Action dated Dec. 29, 2016", 12 pgs.

"U.S. Appl. No. 14/087,094, Notice of Allowance dated Jul. 6, 2017", 5 pgs.

"U.S. Appl. No. 14/087,094, Response filed Mar. 29, 2017 to Non Final Office Action dated Dec. 29, 2016", 17 pgs.

"U.S. Appl. No. 14/087,094, Response filed Jun. 12, 2017 to Final Office Action dated Apr. 28, 2017", 11 pgs.

"U.S. Appl. No. 14/087,094, Response filed Sep. 14, 2016 to Restriction Requirement dated Jul. 27, 2016", 7 pgs.

"U.S. Appl. No. 14/087,094, Restriction Requirement dated Jul. 27, 2016", 6 pgs.

\* cited by examiner

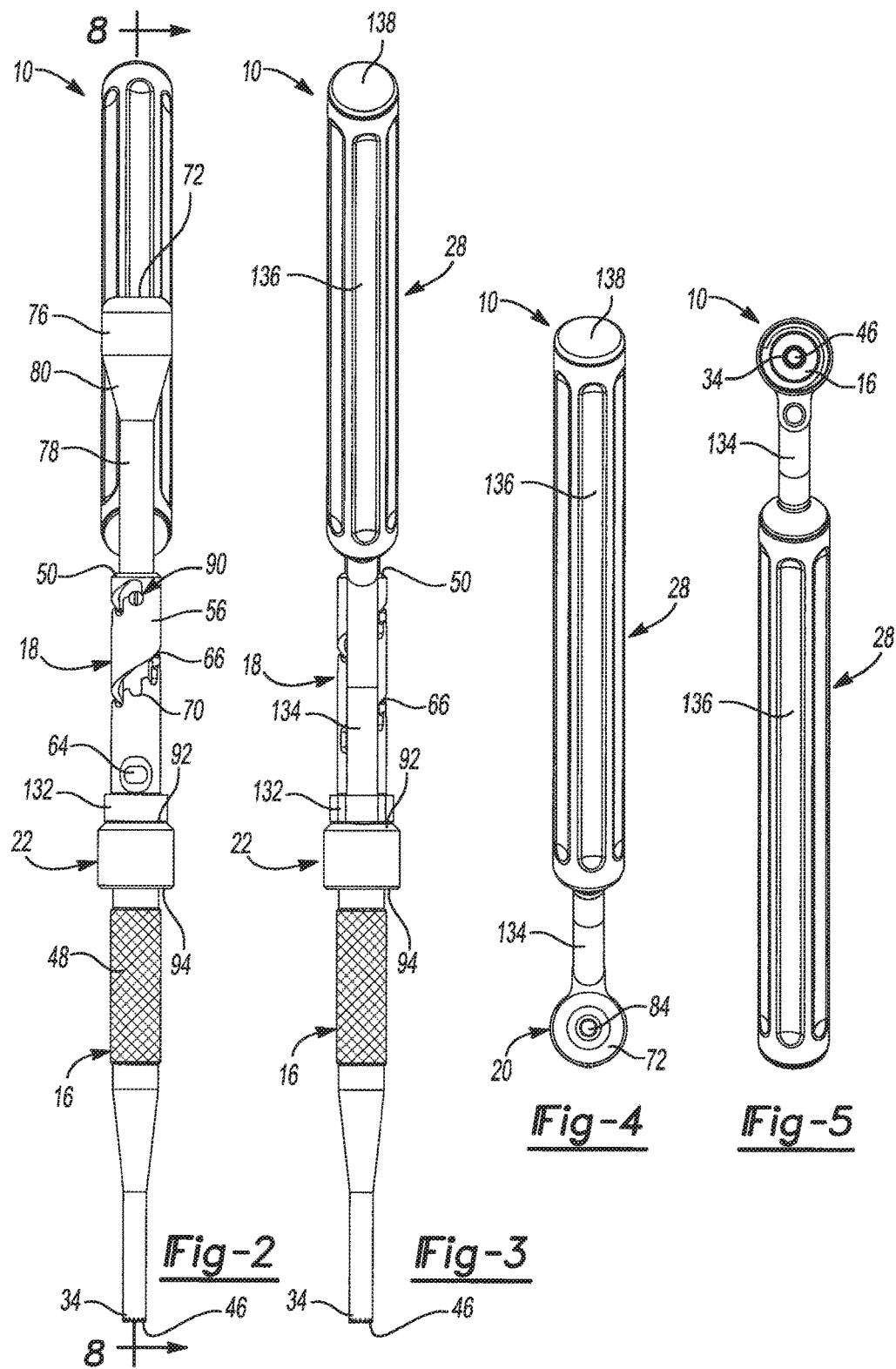

ADJUSTABLE DRILL DEPTH GUIDE

CROSS-REFERENCE TO RELATED APPLICATIONS

This application claims the benefit of U.S. Provisional Application No. 61/731,663, filed on Nov. 30, 2012. The entire disclosure of the above application is incorporated herein by reference.

FIELD

The present disclosure relates to an adjustable drill depth guide, and more particularly to a device and method for adjusting the depth of a drill bit into a bone.

BACKGROUND

This section provides background information related to the present disclosure which is not necessarily prior art.

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue or correct the deformity, which can require the use of one or more orthopedic prosthesis, such as orthopedic nails, screws, implants, etc. For example, in order to restore function to or correct a deformity of the spinal column, one or more implants can be coupled to each vertebral body and interconnected via a suitable device. Implants or anchors can be coupled to each vertebral body, and a connecting device, such as a rod, can be coupled to each of the anchors to stabilize or fix the vertebral bodies relative to each other. Generally, multiple anchors or bone screws can be attached to each vertebral body so that multiple rods can be used to stabilize the spinal column. Holes of various depths may be drilled in the vertebral bodies to prepare the bone to receive the bone screws.

SUMMARY

This section provides a general summary of the disclosure, and is not a comprehensive disclosure of its full scope or all of its features.

The present teachings relate to an instrument for use in preparing a bone to receive a bone screw. More specifically, the present teachings relate to a drill depth guide that can be quickly and easily adjusted to achieve a desired drill depth.

According to one particular aspect, the present disclosure provides an adjustable drill depth guide. The adjustable drill depth guide includes a first sleeve, a second sleeve, a third sleeve, and a biasing member. The first sleeve includes a longitudinal axis, a first proximal end, a first distal end, a first longitudinal bore extending from the first proximal end to the first distal end, a helical slot disposed about the longitudinal axis, and a plurality of notches extending axially from the helical slot. The second sleeve is at least partially disposed within the first longitudinal bore, and extends along the longitudinal axis from a second proximal end to a second distal end. The second sleeve includes a second longitudinal bore and a radially extending stop member. The radially extending stop member is selectively engageable with at least one notch of the plurality of notches. The third sleeve includes a third proximal end, a third distal end, and a third longitudinal bore extending from the third proximal end to the third distal end. The third sleeve is concentrically disposed relative to the first sleeve. The biasing member is disposed substantially adjacent to an outer wall of the third sleeve and biases the second proximal end in the direction of the third distal end.

According to another particular aspect, the present disclosure provides an adjustable drill depth guide. The adjustable drill depth guide includes a first sleeve, a second sleeve, and stop member. The first sleeve includes a longitudinal axis and defines a helical slot disposed about the longitudinal axis. The second sleeve is concentrically arranged relative to the first sleeve and is axially adjustable relative to the first sleeve for adjusting a length of the adjustable drill depth guide. The stop member extends radially from the second sleeve and is disposed in the helical slot. The stop member is selectively received at various positions along the helical slot to positively locate the second sleeve relative to the first sleeve in the axial direction.

According to yet another particular aspect, the present disclosure provides a method of adjusting the length of a drill depth guide. The method includes providing an adjustable drill depth guide that includes a first sleeve having a helical slot, a second sleeve at least partially disposed within the first sleeve, a radially extending stop member coupled to the third sleeve and operably disposed within the helical slot, and a biasing member biasing a distal end of the second sleeve in a first axial direction. The method also includes moving the radially extending stop member in a second axial direction opposite the first axial direction. The method further includes rotating the second sleeve relative to the first sleeve to move the radially extending stop member in at least one of the first axial direction and the second axial direction.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a front view of the adjustable drill depth guide of FIG. 1.

FIG. 3 is a rear view of the adjustable drill depth guide of FIG. 1.

FIG. 4 is a bottom view of the adjustable drill depth guide of FIG. 1.

FIG. 5 is a front view of the adjustable drill depth guide of FIG. 1.

Corresponding reference numerals indicate corresponding parts throughout the several views of the drawings.

DETAILED DESCRIPTION

Figure 1:
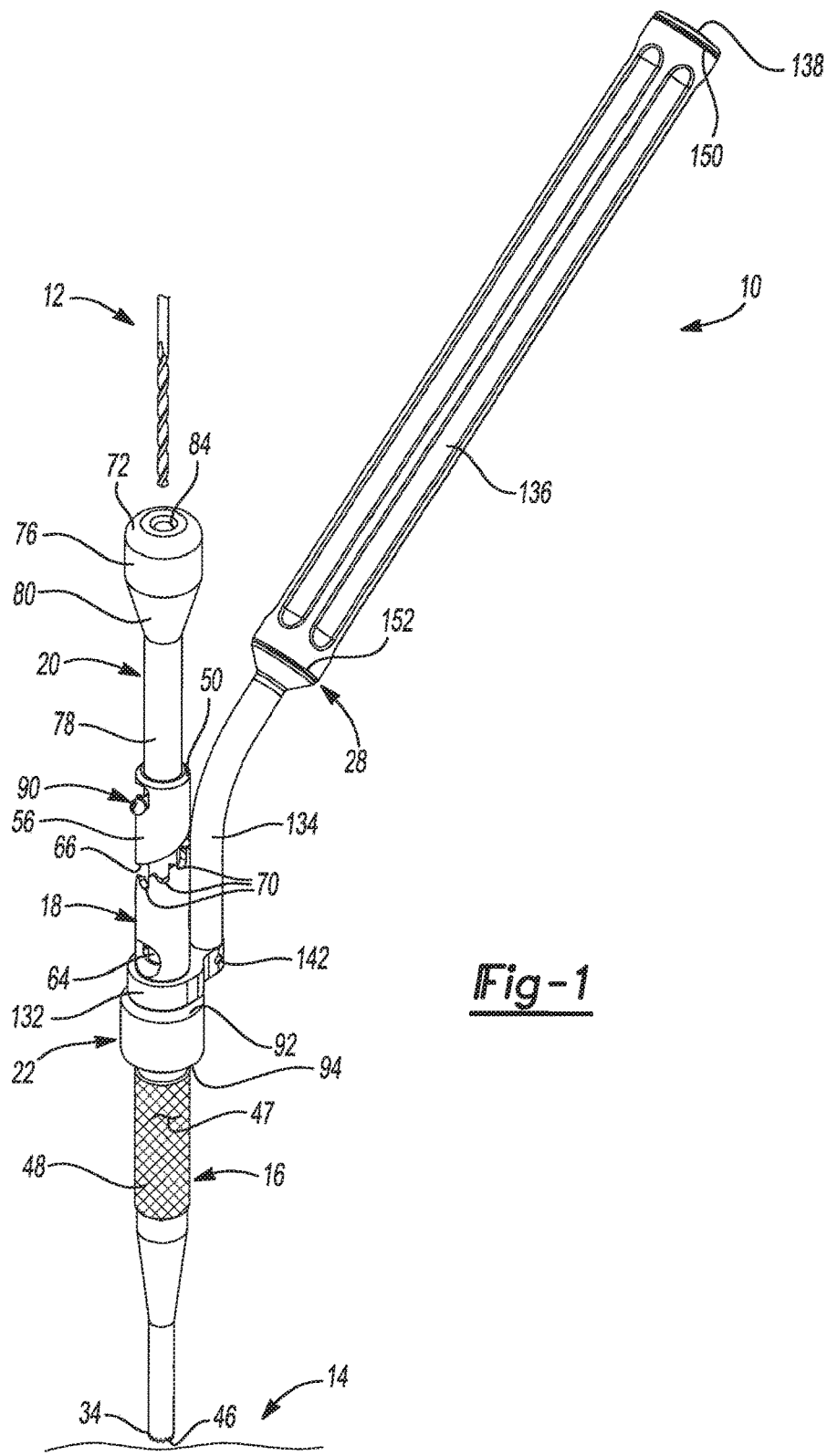
FIG. 1 is a perspective view of an adjustable drill depth guide constructed in accordance with the teachings of the present disclosure.
Figure 6:
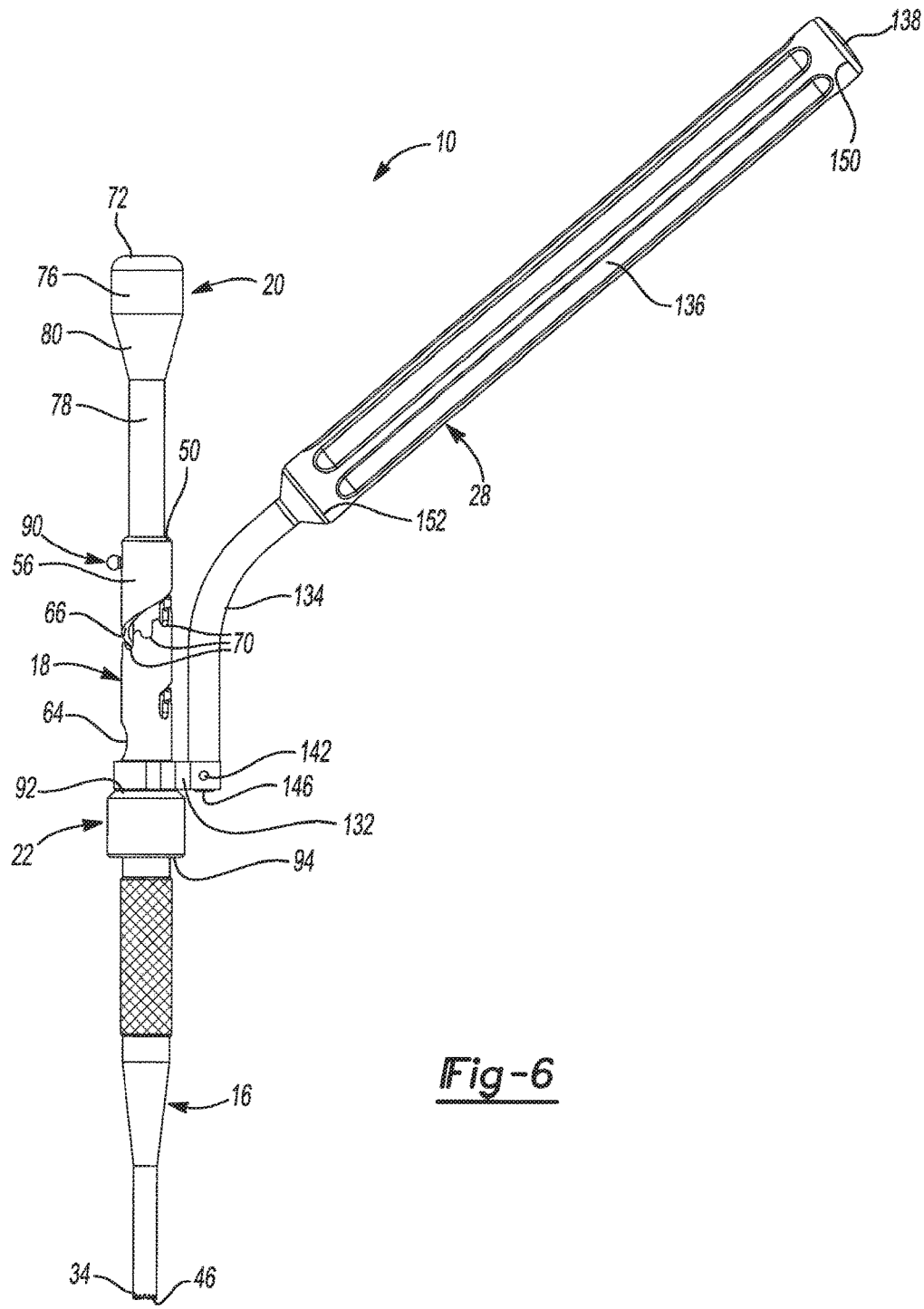
FIG. 6 is a side view of the adjustable drill depth guide of FIG. 1.
Figure 7:
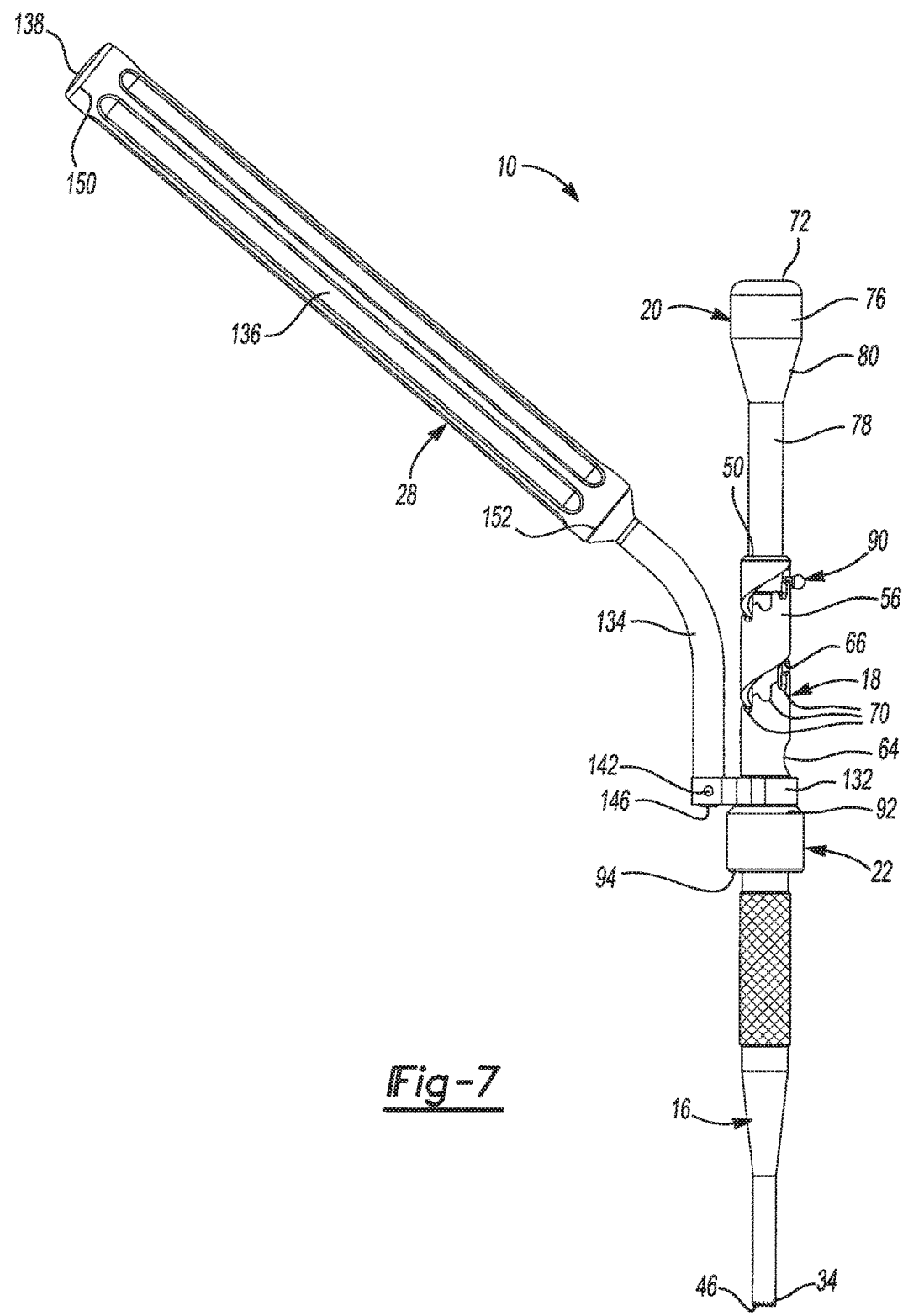
FIG. 7 is another side view of the adjustable drill depth guide of FIG. 1.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-9, an adjustable drill depth guide assembly constructed in accordance with the present teachings is illustrated and identified at reference character 10. The adjustable drill depth guide assembly 10 may be used to control the depth by which a tap or drill bit 12 penetrates a bone 14. According to one exemplary use, the adjustable drill depth guide assembly 10 may be particularly adapted for use in spinal fixation procedures. It will also be appreciated, however, that the present teachings may be adapted to control the penetration depth of a drill bit into any type of material or component.

The adjustable drill depth guide assembly 10 may generally include a tip or end sleeve 16, a control sleeve 18, an adjustment sleeve 20, a collar 22, an inner sleeve 24, a biasing member 26, and a handle assembly 28. As illustrated, the end sleeve 16, the control sleeve 18, the adjustment sleeve 20, the collar 22, and the inner sleeve 24 may together define a guide barrel 25 having a longitudinal axis 30 that accepts the drill bit 12.

Figure 8:
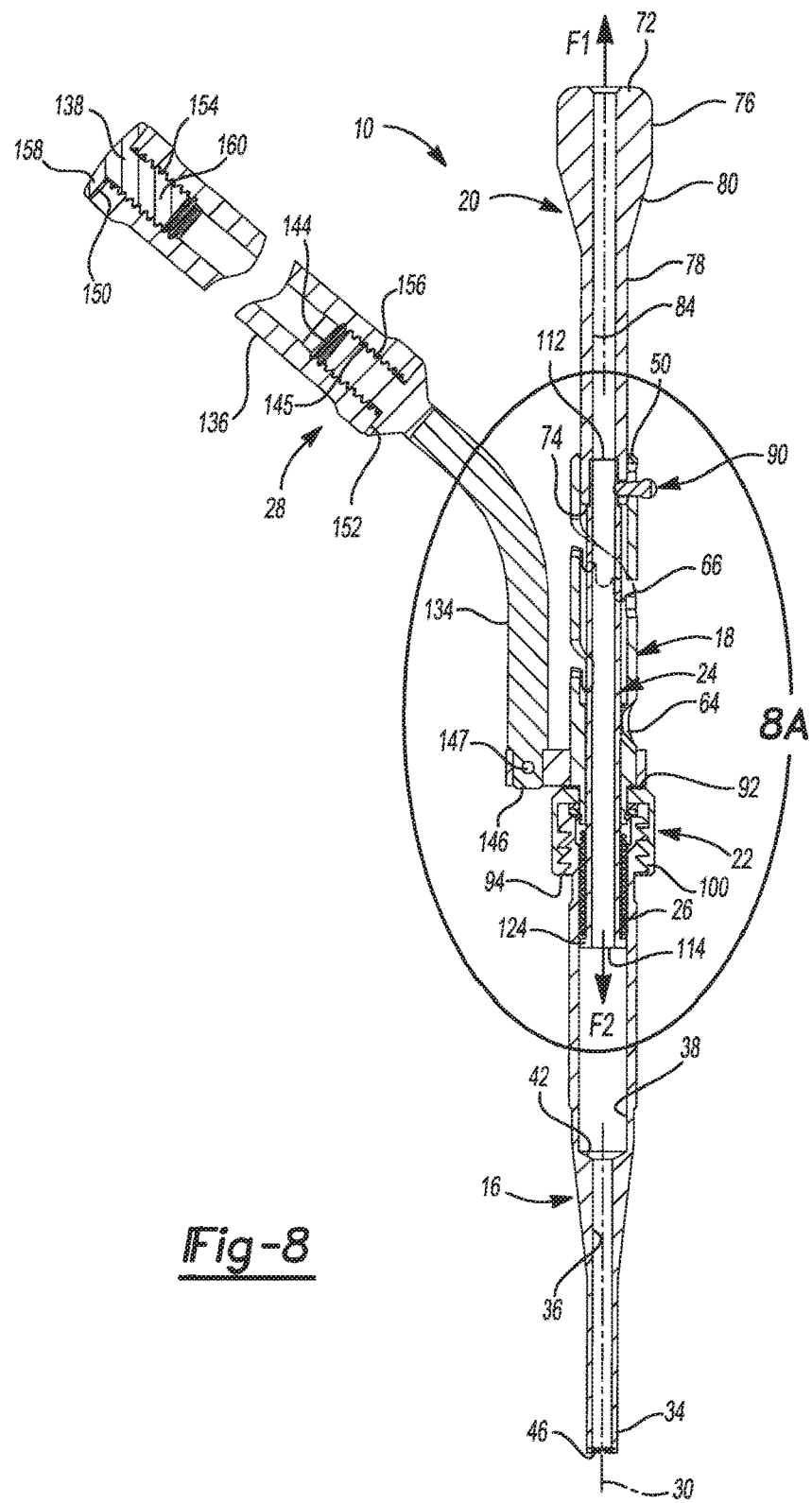
FIG. 8 is a cross sectional view of the of the adjustable drill depth guide of FIG. 1 taken along line 8-8 of FIG. 2.
Figure 8A:
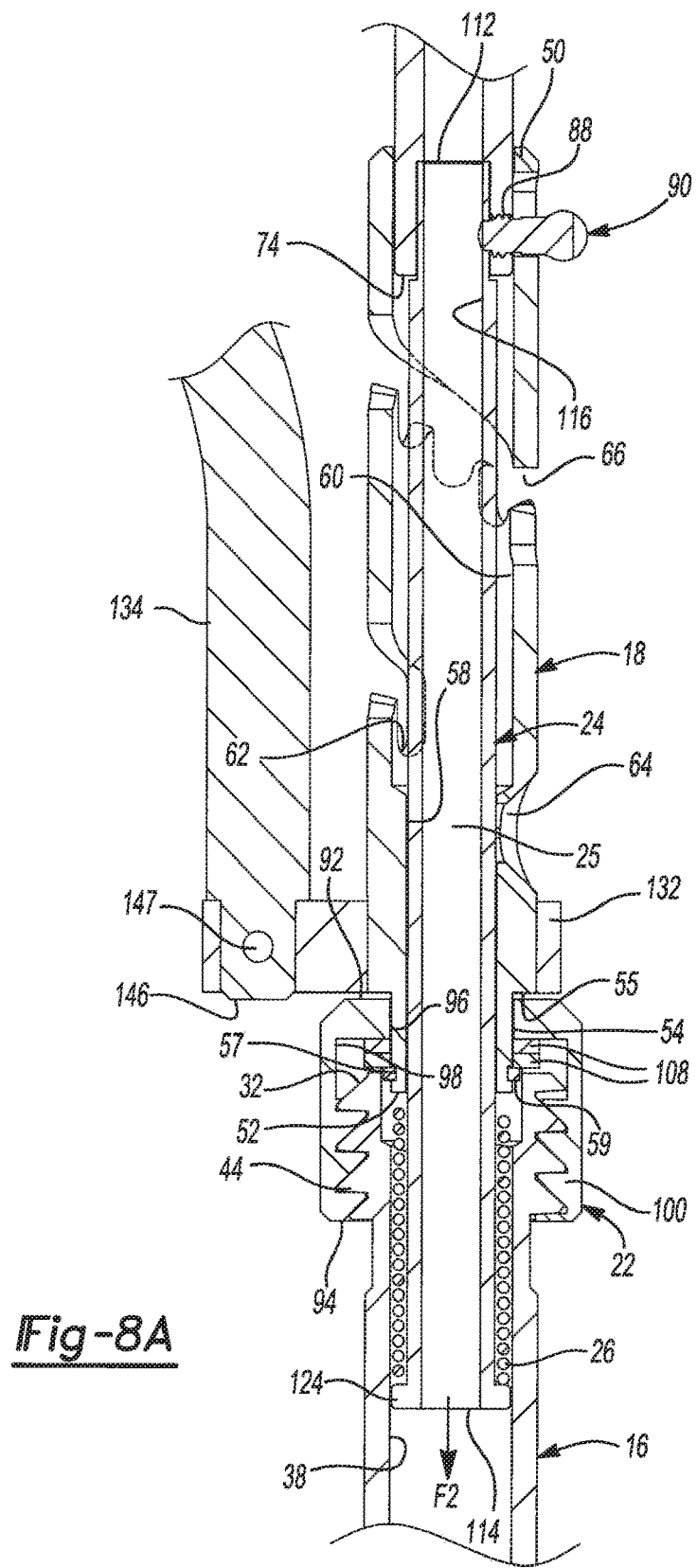
FIG. 8A is a close-up view of area 8A of FIG. 8.
Figure 9:
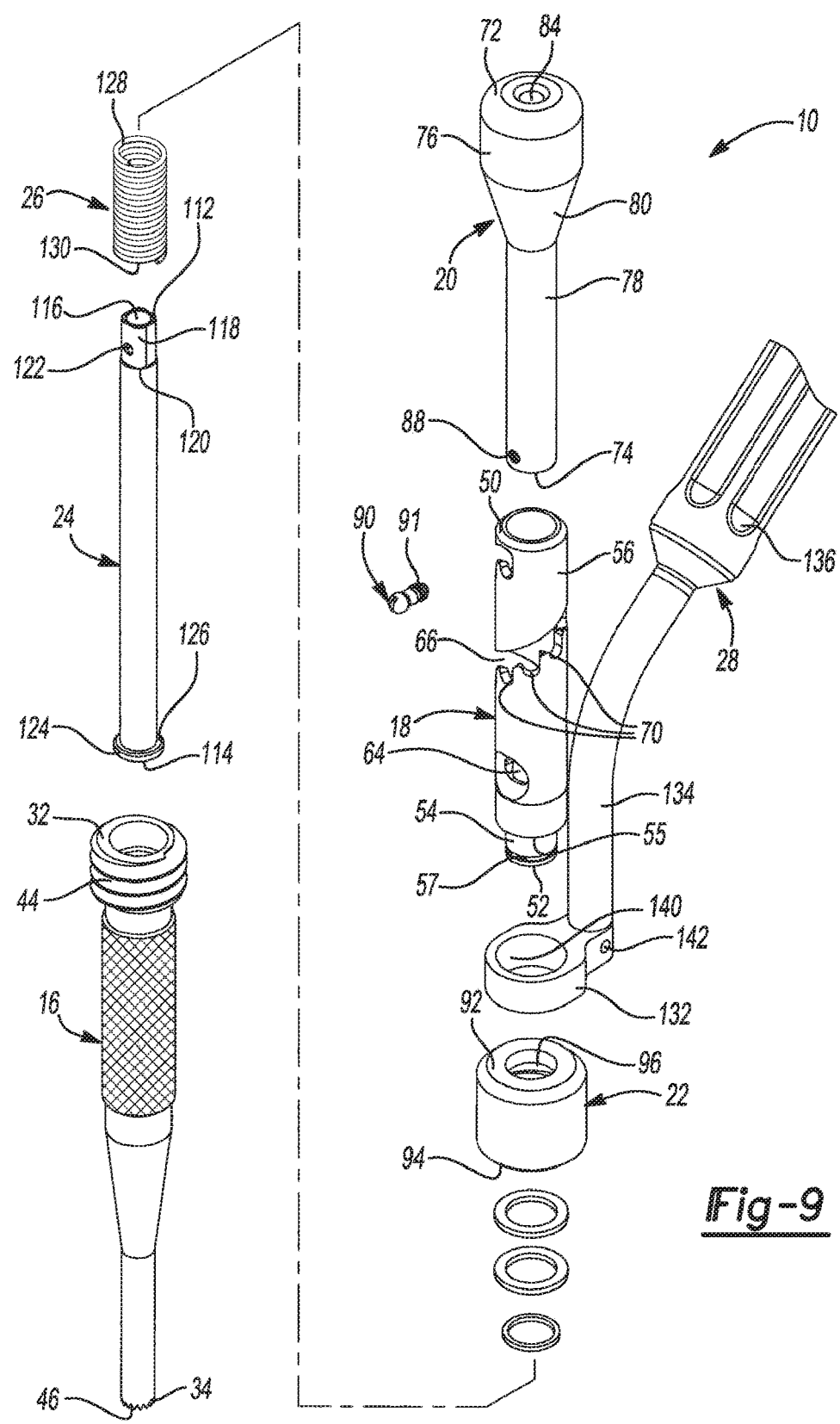
FIG. 9 is an exploded view of the adjustable drill depth guide of FIG. 1.

As illustrated in FIGS. 8 and 8A, the end sleeve 16 may extend between a proximal end 32 and a distal end 34 along the longitudinal axis 30, and may include a bore 36, and a counterbore 38. The bore 36 may extend between the proximal end 32 and the distal end 34 of the end sleeve 16. The counterbore 38 may extend longitudinally from the proximal end 32. As illustrated, an annular surface 42 extending between and connecting the bore 36 and the counterbore 38 may be tapered or chamfered to generally guide the drill bit 12 along the longitudinal axis 30 and in the direction of the bone 14.

The proximal end 32 of the end sleeve 16 may include an externally threaded portion 44. The distal end 34 of the end sleeve 34 may include a toothed portion 46 having a plurality of axially extending teeth. The toothed portion 46 may help to secure the placement of the adjustable drill depth guide assembly 10 relative to the bone 14 or other working surface. An outer surface 47 of the end sleeve 16 may include a knurled portion 48 to allow a user to better grip and maneuver the adjustable drill depth guide assembly 10.

The control sleeve 18 may extend between a proximal end 50 and a distal end 52 along the longitudinal axis 30. The control sleeve 18 may include a generally cylindrical neck portion 54 and a generally cylindrical body portion 56. The body portion 56 may extend longitudinally from the proximal end 50 of the control sleeve 18 to a distal end 55 of the body portion 56. The neck portion 54 may be integrally and concentrically formed with the body portion 56 and may extend longitudinally from the distal end 55 of the body portion 56 to the distal end 52 of the control sleeve 18. The neck portion 54 may have a smaller diameter than the body portion 56 and may include an annular groove 57. The annular groove 57 may support a retaining ring 59. In an assembled configuration, the neck portion 54 may be concentrically and rotatably disposed within the counterbore 38 of the end sleeve 16.

A bore 58 may extend longitudinally from the proximal end 50 to the distal end 52 of the control sleeve 18. A counterbore 60 may extend longitudinally from the proximal end 50 to a location between the proximal end 50 and the distal end 52 of the control sleeve 18. An annular surface 62 may extend between and connect the bore 58 and the counterbore 60. As will be explained in more detail below, the annular surface 62 may be tapered or chamfered and may prevent axial displacement of the adjustment sleeve 20 relative to the control sleeve 18 in an assembled configuration.

The body portion 56 of the control sleeve 18 may include an aperture 64 and a helical slot 66. The aperture 64 may extend laterally through the sidewall of the control sleeve 18 to allow a user to view the inner sleeve 24 within the bore 58. It will be appreciated that the helical slot 66 may extend around the periphery of the control sleeve 18 any number of revolutions, or fractions thereof, within the scope of the present teachings. In one configuration, the helical slot 66 extends approximately seven hundred twenty degrees around the control sleeve 18. The helical slot 66 may include a plurality of axially extending notches 70. The notches 70 may extend axially in the direction of the distal end 52 of the control sleeve 18, such that the lower edge (relative to the view in FIG. 1, for example) of the helical slot 66 has a generally scalloped or waved configuration. In one configuration, the axial distance between adjacent notches 70 may be approximately 2 millimeters.

The adjustment sleeve 20 may extend between a proximal end 72 and a distal end 74 along the longitudinal axis 30. The proximal end 72 of the adjustment sleeve 20 and the distal end 34 of the end sleeve 16 may generally define a length of the drill depth guide 10 along the longitudinal axis 30, and thus the distance by which the drill bit 12 extends beyond the distal end 34 of the end sleeve 16. The adjustment sleeve 20 may include a generally cylindrical head portion 76 and a generally cylindrical stem portion 78. The head portion 76 may have a larger diameter than the stem portion 78. A generally frustoconical intermediate portion 80 may extend between and connect the head portion 76 and the stem portion 78. While the adjustment sleeve 20 is described herein as including a generally cylindrical head portion 76, a generally cylindrical stem portion 78, and generally frustoconical intermediate portion 80 therebetween, it will be appreciated that the head portion 76, the stem portion 78 and the intermediate portion may have other geometries within the scope of the present teachings. The head portion 76 may be integrally formed with the stem portion 78 and the intermediate portion 80 as a monolithic construct.

The adjustment sleeve 20 may further include a bore 84 and a aperture 88. The bore 84 may extend longitudinally from the proximal end 72 to the distal end 74 of the adjustment sleeve 20. The aperture 88 may extend laterally through the sidewall of the stem portion 78 of the adjustment sleeve 20.

In an assembled configuration, the stem portion 78 of the adjustment sleeve 20 may be concentrically and rotatably disposed with the bore 58 of the control sleeve 18. A radially extending stop member, such as a pin 90, may extend through the helical slot 66 and into engagement with the aperture 88. In one configuration, the aperture 88 may be internally threaded and the pin 90 may include an externally threaded portion 91, such that rotating the pin 90 with a screwdriver (not shown) or other suitable tool will threadably engage the pin 90 with the aperture 88. In other configurations, the pin 90 may be secured within the aperture 88 by utilizing a press-fit engagement, an adhesive, or other suitable technique. In one configuration, the pin 90 is permanently coupled within the aperture 88 using a press-fit engagement.

The collar 22 may extend between a proximal end 92 and a distal end 94 along the longitudinal axis 30. While the collar 22 is generally illustrated as a cylindrical member, it will be appreciated that the collar 22 may have other geometries within the scope of the present teachings. The collar 22 may include a bore 96 and a counterbore 98. The bore 96 may extend longitudinally through the collar 22 from the proximal end 92 to the distal end 94. The counterbore 98 may extend longitudinally from the distal end 94 to a location between the proximal end 92 and the distal end 94 of the control sleeve 18, and may include an internally threaded portion 100.

In the assembled configuration, the collar 22 may be concentrically disposed around the end sleeve 16 and the control sleeve 18. As illustrated, the threaded portion 100 of the collar 22 may engage the threaded portion 44 of the end sleeve 16, so that the end sleeve 16 can be removed from the collar 22 for cleaning or otherwise servicing the assembly 10. The neck portion 54 of the control sleeve 18 may be concentrically disposed within the collar 22 such that the bore 96 abuts the neck portion 54 of the control sleeve 18, and the proximal end 92 of the collar 22 abuts the end 55 body portion 56 of the control sleeve 18.

The guide assembly 10 may further include at least one washer 108. In one configuration, the guide assembly includes two washers 108. As illustrated, in the assembled configuration, the washers 108 may be axially disposed between the counterbore 98 of the collar 22 and the proximal end 32 of the end sleeve 16. The neck portion 54 of the control sleeve 18 may be concentrically disposed within the washers 108, such that the retaining ring 59 engages the axial end of the washers 108 and the distal end of the neck portion 54 to prevent axial displacement of the control sleeve 18 relative to the collar 22 and to allow the retaining ring 59 and the control sleeve 18 to rotate relative to the end sleeve 16.

The inner sleeve 24 may extend between a proximal end 112 and a distal end 114 along the longitudinal axis 30. The inner sleeve 24 may be a generally cylindrical member having a bore 116 extending longitudinally therethrough from the proximal end 112 to the distal end 114. The proximal end 112 of the inner sleeve 24 may include a generally cylindrical neck portion 118 defining an axial stop surface 120. The stop surface 120 may be disposed between the proximal end 112 and the distal end 114 of the inner sleeve 24. The neck portion 118 may include a laterally extending aperture 122. The distal end 114 of the inner sleeve 24 may include a radially extending flange or lip 124 defining an axial stop surface 126.

In the assembled configuration the inner sleeve 24 may be concentrically disposed within the end sleeve 16, the control sleeve 18, the adjustment sleeve 20, and the collar 22. The neck portion 118 of the inner sleeve 24 may be disposed within the adjustment sleeve 20 such that the distal end 74 of the adjustment sleeve 20 is disposed adjacent to the stop surface 120 of the inner sleeve 24. The inner sleeve 24 may be fixed for axial displacement with the adjustment sleeve 20. Specifically, in one configuration the pin 90 may extend through the adjustment sleeve 20 and at least partially within the aperture 122 of the inner sleeve 24.

In one configuration, the inner sleeve 24 may include a metering portion (the portion of inner sleeve 24 visible through aperture 62) showing distances such as inches, millimeters, centimeters, etc. The metering portion of the inner sleeve 24 may be visible through the aperture 64 of the control sleeve 18, such that the user can determine the distance by which the drill bit 12 will extend beyond the distal end 34 of the end sleeve 16.

The biasing member 26 may be disposed between the control sleeve 18 and the inner sleeve 24. In one configuration, the biasing member 26 may be a helical compression spring longitudinally extending between a proximal end 128 and a distal end 130. The biasing member 26 may be concentrically disposed around the inner sleeve 24, and concentrically disposed within the counterbore 38 of the end sleeve 16. The proximal end 128 of the biasing member 26 may be disposed adjacent the distal end 52 of the control sleeve 18. The distal end 130 of the biasing member 26 may be disposed adjacent the stop surface 126 of the inner sleeve 24. Accordingly, in the assembled configuration, the biasing member 26 may be operable to bias the inner sleeve 24 and the adjustment sleeve 20 relative to the control sleeve 18. Specifically, the biasing member 26 may be operable to bias the distal end 114 of the inner sleeve 24 away from the distal end 52 of the control sleeve 18, and bias the proximal end 72 of the adjustment sleeve 20 in the direction of the distal end 34 of the end sleeve 16. Accordingly, the biasing member 26 may be operable to bias the pin 90 into engagement with at least one of the notches 70 of the helical slot 66.

The handle assembly 28 may include a collar 132, a shaft 134, a handle 136, and a cap 138. The collar 132 may define a longitudinally extending bore 140 and an aperture 142. In an assembled configuration, the control sleeve 18 may be concentrically disposed within the bore 140, such that the handle assembly 28 can be rotated or otherwise maneuvered independently of the end sleeve 16.

The shaft 134 may extend in a generally arcuate configuration from a proximal end 144 to a distal end 146. In one configuration, the shaft 134 may be constructed from aluminum to improve the weight and strength characteristics of the shaft 134. It will also be appreciated that the shaft 134 may be constructed from any other similarly suited material. The proximal end 144 of the shaft 134 may include an externally threaded portion 145. The distal end 146 of the shaft 134 may be mounted to the collar 132, and may include an aperture 147. In one configuration, the aperture 147 of the shaft 134 may be aligned with the aperture 142 of the collar. A pin may be disposed within the aperture 147 and the aperture 142 to secure the shaft 134 to the collar 132. It will also be appreciated that the shaft 134 may be mounted to the collar 132 using other methods and configurations within the scope of the present teachings.

The handle 136 may extend from a proximal end 150 to a distal end 152. In one configuration, the handle 136 is formed from silicone to allow a user to better grip the handle 136. It will also be appreciated that the handle 136 may be formed from any other similarly suited material. The proximal end 150 of the handle 136 may include a first internally threaded portion 154. The distal end 152 of the handle 136 may include a second internally threaded portion 156. The proximal end 144 of the shaft 134 may be mounted to the handle 136 such that the threaded portion 145 of the shaft 134 is threadably engaged with the second threaded portion 156 of the handle 136. It will also be appreciated that the handle 136 may be mounted to the shaft 134 using a press-fit engagement, adhesive, or any other suitable technique.

The cap 138 may include a head portion 158 and a stem portion 160. The stem portion 160 may be externally threaded, such that the cap 138 can be mounted to the handle 136 by threadably engaging the stem portion 160 with the threaded portion 154 of the handle.

To adjust the depth by which a drill bit 12 extends beyond the distal end 34 of the end sleeve 16, the user may apply an axial force F1 to the adjustment sleeve 20 to overcome a compressive biasing force F2 of the biasing member 26, as illustrated in FIGS. 8 and 8A. The force F1 may cause the proximal end 72 of the control sleeve 72 to travel away from the distal end 34 of the end sleeve 16, and cause the pin 90 to disengage the notch 70, such that the pin 90 is disposed within the helical slot 66 of the control sleeve 18. The user may then rotate the adjustment sleeve 20 about the longitudinal axis 30 relative to the control sleeve 18, such that the pin 90 traverses the helical slot 66, and the proximal end 72 of the adjustment sleeve 20 travels in the axial direction relative to the distal end 34 of the end sleeve 16. To secure the depth by which a drill bit 12 extends beyond the distal end 34 of the end sleeve 16, the user may release the axial force F1, such that the biasing force F2 causes the pin 90 to travel in the axial direction and into engagement with one of the notches 70, thus preventing the adjustment sleeve 20 from rotating relative to the control sleeve 18.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of adjusting a length of a drill depth guide, the method comprising:
    providing an adjustable drill depth guide comprising:
        a first sleeve having a helical slot;
        a second sleeve at least partially disposed within the first sleeve, the second sleeve having a proximal end;
        a radially extending stop member coupled to the second sleeve and operably disposed within the helical slot;
        a surface-contacting sleeve rotatably coupled to the first sleeve and axially locked with the first sleeve, the surface-contacting sleeve having a distal end; and
        a biasing member biasing the second sleeve in a first axial direction of the surface-contacting sleeve, wherein the biasing member biases the second sleeve in the first axial direction toward the distal end of the surface-contacting sleeve;
    moving the radially extending stop member in a second axial direction opposite the first axial direction; and
    rotating the second sleeve relative to the first sleeve to move the radially extending stop member in a least one of the first axial direction and the second axial direction to change a distance between the proximal end and the distal end.

2. The method of claim 1, wherein moving the radially extending stop member further comprises axially moving the second sleeve within the surface-contacting sleeve.

3. The method of claim 2, wherein the second sleeve includes an inner sleeve coupled to the second sleeve within the first sleeve, the inner sleeve extending into the surface-contacting sleeve.

4. The method of claim 1, further comprising rotating the first sleeve relative to the surface-contacting sleeve independently of the axial location of the second sleeve.

5. The method of claim 4, wherein rotating the first sleeve relative to the surface-contacting sleeve further comprises rotating the first sleeve relative to the surface-contacting sleeve while the surface-contacting sleeve is engaged with a surface.

6. The method of claim 5, further comprising pushing the distal end of the surface-contacting sleeve into engagement with the surface via pushing the first sleeve axially against the surface-contacting sleeve via a retaining ring.

7. The method of claim 6, further comprising rotating and pushing the first sleeve relative to the surface-contacting sleeve using a handle connected to the first sleeve.

8. The method of claim 1, wherein rotating the second sleeve relative to the first sleeve comprises rotating the second sleeve relative to the first sleeve independently of the first sleeve rotating relative to the surface-contacting sleeve.

9. The method of claim 1, further comprising simultaneously rotating the second sleeve and the first sleeve relative to the surface-contacting sleeve.

10. The method of claim 1, wherein moving the radially extending stop member further comprises moving the second sleeve within the first sleeve to show distances located on a metering portion of the second sleeve in an aperture located on the first sleeve.

11. The method of claim 1, wherein moving the radially extending stop member further comprises engaging the radially extending stop member with a notch on the helical slot to limit biasing of the biasing member.

12. A method of adjusting an adjustable drill depth guide, the method comprising:
   engaging a distal end of a surface-contacting sleeve with a surface, the surface-engaging sleeve defining a drill axis;
   moving a handle connected to a control sleeve to rotate the control sleeve relative to the surface-contacting sleeve and to position the drill axis; and
   adjusting an axial position of an adjustment sleeve relative to the control sleeve to define an overall length of the adjustable drill depth guide along the drill axis.

13. The method of claim 12, wherein moving the handle connected to the control sleeve comprises rotating the control sleeve against a retaining ring coupling the control sleeve to the surface-contacting sleeve.

14. The method of claim 13, wherein rotating the control sleeve against the retaining ring further comprises inhibiting axial movement between the control sleeve and the surface-contacting sleeve.

15. The method of claim 12, wherein adjusting the axial position of the adjustment sleeve relative to the control sleeve comprises:
   overcoming a spring force of a biasing mechanism; and
   moving a radially extending stop member in a slot on the control sleeve.

16. The method of claim 15, wherein adjusting the axial position of the adjustment sleeve relative to the control sleeve further comprises aligning depth indicia on the adjustment sleeve with a window on the control sleeve.

17. The method of claim 12, further comprising attaching an inner sleeve to the adjustment sleeve for sliding within the surface-contacting sleeve.

18. A method of adjusting a length of a drill depth guide, the method comprising:
   engaging a distal end of a surface-contacting sleeve with a surface;
   positioning a control sleeve connected to the surface-contacting sleeve;
   adjusting an axial position of an adjustment sleeve relative to the control sleeve to define an overall length of the adjustable drill depth guide along the drill axis;
   viewing a metering portion of the adjustment sleeve through an aperture in the control sleeve to provide a showing of a drill distance of a drill bit beyond the distal end of surface-contacting sleeve; and
   simultaneously rotating the control sleeve and the adjustment sleeve relative to the surface-contacting sleeve.

19. The method of claim 18, further comprising inserting a drill bit into the drill depth guide such that a length of the drill bit extending from the surface-contacting sleeve equals a depth indicated by the depth indicia.

* * * * *